Oct. 17, 1967 L. E. GAVELLO Plant Pat. 2,772
VERONICA PLANT
Filed April 25, 1966
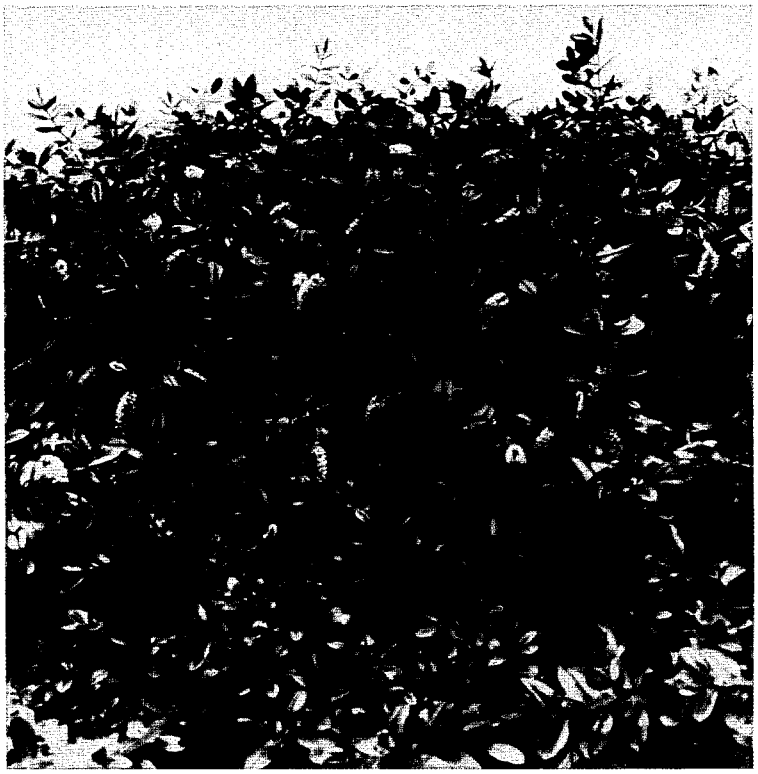
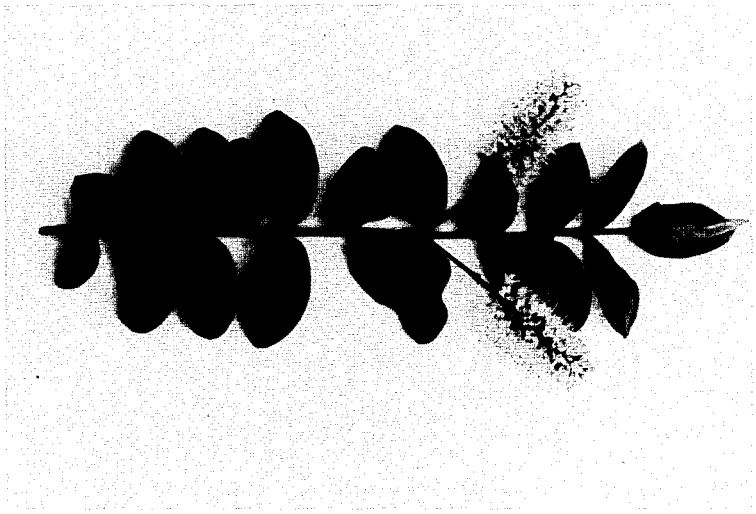

United States Patent Office

Plant Pat. 2,772
Patented Oct. 17, 1967

2,772
VERONICA PLANT

Louis E. Gavello, 3436 Maricopa Ave.,
Richmond, Calif. 94804

Filed Apr. 25, 1966, Ser. No. 545,169
1 Claim. (Cl. Plt.—54)

My invention relates to a new and distinct variety of Hebe (Veronica) plant.

This new and distinct variety was discovered by me as a newly found seedling in a cultivated area under a group of oak trees in the San Francisco Zoo, Calif., in June 1962, and my attention was drawn to the plant by its low growing and spreading characteristics, its compact habit and robust appearance with thick foliage distinguishing the plant from known conventional varieties. No one of about 25 local nurserymen, including the gardener foreman of the zoo, could identify the specie.

Following my initial discovery, I promptly took steps to preserve and observe the new seedling, as well as to asexually reproduce the same by cuttings in June 1962, as performed by me at my nursery in Richmond, Calif. Continued observations of the original seedling and the asexual reproductions thereof have fully demonstrated that the aforementioned characteristics and distinctions are firmly established and are transmissible by asexual reproduction. Approximately 50 asexual reproductions have been made and cuttings are now being taken from the fourth generation.

Among the outstanding characteristics of the new variety, the following features, as observed of a mature bush, contribute to the novelty and distinctiveness thereof, and represent a unique combination which is definitely different from that of any other variety of Hebe plant of which I am aware:

(1) Bush is of low height, compact, of very wide spread and of moderate growth;

(2) Branches are substantially straight, with side laterals on main branches varying in length, being largest at base to small at tip of main branch, some laterals being located opposite each other and others alternate, and with many side branches growing from the laterals;

(3) Leaves are sessile and opposed to each other in pairs with the pairs of leaves on a branch all lying substantially in the same plane thereon, and with the leaves at the tip of the branch disposed in a plane at right angles thereto;

(4) Blooms are profuse, there being many racemes at the end of each branch, the racemes being tapered, long and arched; the florets on racemes opening initially from base to tips, are white as they open with many having a light lavender blush; the buds initially all green have their tips turn white, progressing towards base of bud as bud opens into white floret.

The accompanying drawing shows in separate views a typical bush of my new variety of Hebe plant in bloom and a branch bearing a number of racemes and leaves, and as depicted in color as nearly true as it is reasonably possible to make the same in a color illustration of this character.

The following is a detailed description of the new variety, with color terminology in accordance with Maerz and Paul, A Dictionary of Color, 2nd edition, 1950.

Parentage: Newly found seedling of unknown parentage.
Classification: Botanic—Hebe (Veronica).
Propagation: Holds its distinguishing characteristics through succeeding propagations by cuttings.
Locality where grown and observed: Richmond, Calif.
Form: Bush—prostrate, approximately 12 inches to 16 inches tall, compact, with an approximately 6 foot spread; vigorous and very robust with thick foilage.

Rate of growth: 2½ foot spread in 2 years from ground planting.
Time to maturity: 3 to 3½ years.
Branches: Main branches approximately 3 feet; side laterals vary from approximately 2 feet at base of plant to small laterals at tip of main branch; some laterals are located opposite each other and others alternate; many side branches grow from laterals. Color—Cordovan (Woodland Brown), Plate 8: H–8.

Foliage:
*Leaves.*—Evergreen; glabrous only on upper side; smooth; thick; elliptic obovate; sessile.
*Length of leaves.*—Approximately 2 to 2¼ inches.
*Width of leaves.*—Approximately 1 to 1¼ inches at widest portion.
*Rib.*—Prominent mid-rib on reverse side, full length of leaf.
*Leaf arrangement.*—Opposite in pairs; in same plane on branch; pairs of leaves at terminal end of branch generally in plane at right angles to the plane of the leaves on remainder of branch.
*Color.*—Upper side, Polo Green, Plate 23: J–9. Lower side, Fern Green, Plate 21: F–5.

Flower:
*Blooms.*—Reaches full bloom in August in Richmond, Calif.; some flowers and color for most of the year around; repeat.
*Racemes.*—Single on a peduncle; compact, axillary compound; conical elongated, bowed and arching downwardly with base of raceme approximately 1 inch from juncture of peduncle with leaf jointure to branch.
*Length.*—In flower, approximately 2½ to 3½ inches.
*Width at base.*—Approximately ¾ to ⅞ inch.
*Number.*—Approximately 6 at end of each branch when bush is in full bloom.
*Buds.*—Compact; vary in size from base to tip; each bud is on a small stem (pedicel). Color—green unopened, Plate 20: I–6, becoming white tipped progressing towards base of bud as bud opens into white floret.
*Florets.*—Stalked on peduncle; initially white in color with some having a light lavender blush.
*Form.*—Tubular with slight outward flare at top generally with three fluted erect petals; length from base of calyx to tip of petals approximately ¼ inch; pistil and stamens extending beyond tip of petals approximately ⅛ to 3/16 inch; anthers brown.
*Number.*—Approximately 75 to 95 florets to each raceme.

Weather resistance: Coastal areas of California; exposure to sun—not recommended; exposure to wind—some.
Disease resistance: Very disease resistant.
Other characteristics: Will grow in most types of soil.

Having described and illustrated my new variety of Hebe (Veronica) plant, I claim:

A new and distinct variety of Hebe (Veronica) plant, substantially as illustrated and described, characterized as to novelty by:

(a) the compact, prostrate form of the plant having a low height and an exceedingly wide spread, being vigorous and very robust with thick foliage, (b) the paired, spaced arrangement of the leaves on each branch lying in the same plane with the leaves at the tip of the branch disposed generally in a plane at right angles thereto, (c) the profuse grouping of elongated conical shaped compound racemes, each generally downwardly arched and each on a separate peduncle at the end of each branch, (d) the buds becoming white tipped and progressing downwardly towards the base of the buds and opening to white florets, some having a slight lavender blush, (e) the dark green color of its leaves of large size and generally elliptic obovate in shape contrasting with the white color of its flowers, (f) the elongated tubular form of the florets of the racemes, (g) its resistance to disease, (h) its ability to grow in most types of soil and (i) its moderate growth and suitability for garden decorative purposes coming to full bloom in late summer and bearing flowers the year around.

No references cited.

ABRAHAM G. STONE, *Primary Examiner.*

ROBERT E. BAGWILL, *Examiner.*